US006581780B1

(12) United States Patent
Jakob et al.

(10) Patent No.: US 6,581,780 B1
(45) Date of Patent: Jun. 24, 2003

(54) AUTOMATIC GRADATION UNIT

(75) Inventors: Herbert E. Jakob, Chattanooga, TN (US); Michael E. Barrett, Lula, GA (US); Gary P. Heeszel, Eugene, OR (US); David F. Peaks, Eugene, OR (US)

(73) Assignee: AI Enterprises, Inc., Morris, MN (US)

( * ) Notice: Subject to any disclaimer, the term of this patent is extended or adjusted under 35 U.S.C. 154(b) by 101 days.

(21) Appl. No.: 09/758,992

(22) Filed: Jan. 16, 2001

(51) Int. Cl.⁷ .................................................. B07B 1/00
(52) U.S. Cl. ........................................ 209/239; 209/260
(58) Field of Search ........................ 209/10, 239, 592, 209/645, 311, 315, 319, 240, 241, 242, 255, 257, 260

(56) References Cited

U.S. PATENT DOCUMENTS

| | | | |
|---|---|---|---|
| 1,051,267 A | | 1/1913 | Rombauer |
| 3,098,037 A | * | 7/1963 | Tonjes et al. ............... 209/260 |
| 3,297,159 A | | 1/1967 | Heise |
| 3,392,491 A | | 7/1968 | Vogt |
| 3,439,800 A | | 4/1969 | Tonjes |
| 3,690,183 A | * | 9/1972 | Livingood ................. 73/865.5 |
| 3,944,146 A | * | 3/1976 | Stockmann et al. .......... 241/30 |
| 4,299,695 A | | 11/1981 | Bostrom |
| 4,544,102 A | * | 10/1985 | Hahn et al. .............. 241/24.11 |
| 4,667,887 A | * | 5/1987 | Kawaguchi ................ 241/20 |
| 5,059,310 A | | 10/1991 | Fischer |
| 5,222,605 A | | 6/1993 | Pogue |
| 5,275,293 A | | 1/1994 | Crider |
| 5,431,285 A | | 7/1995 | Harbour |
| 5,749,471 A | | 5/1998 | Andersson |
| 5,950,939 A | | 9/1999 | Drinkwater et al. |
| 6,032,886 A | | 3/2000 | Drinkwater et al. |
| 6,431,366 B2 | * | 8/2002 | Fallon ........................ 209/311 |

* cited by examiner

Primary Examiner—Donald P. Walsh
Assistant Examiner—Joseph Rodriguez
(74) Attorney, Agent, or Firm—Chambliss, Bahner & Stophel, P.C.

(57) ABSTRACT

A system for controlling the operation of an item of equipment for processing materials to produce a product which includes aggregate materials of various particle sizes in a predetermined weight ratio includes a sampling device for obtaining a sample of the product from a predetermined location and a gradation assembly. The gradation assembly includes a plurality of gradation screens and a weighing pan for measuring the weight of aggregate material. The gradation screens are supported by a frame in a generally horizontal attitude in a stacked arrangement, so that each screen in the stack has screen openings that are smaller than those of the screen immediately above it in the stack. The assembly also includes a vibrator for vibrating the screens and a mechanism for sequentially depositing the aggregate material that is retained on each screen or that passes through all of the screens in the weighing pan. The system determines the ratios of the weights of the amounts of the aggregate materials that are retained on each of the screens or that passes through all of the screens to the total weight of the sample, and compares each of the ratios so determined to a predetermined standard. The system also adjusts the operation of the item of equipment if the ratio of the weight of the aggregate materials that are retained on any of the screens or that passes through all of the screens to the total weight of the sample fails to meet the predetermined standard.

19 Claims, 8 Drawing Sheets

AUTOMATIC GRADATION UNIT

FIELD OF THE INVENTION

This invention relates generally to controlling the operation of equipment for processing materials to produce an aggregate product having a predetermined weight ratio of particle sizes. In a preferred embodiment of the invention, the gradation of a sample of a crushed stone product is automatically analyzed and the results of such analysis are used to control the operation of the crusher or crushers.

BACKGROUND AND DESCRIPTION OF THE PRIOR ART

Analysis of products comprised of various aggregate materials is commonly required in the construction, mining and aggregate processing industries to insure that the materials meet the required specifications for quality, composition and/or gradation. Many such aggregate products are comprised of mixtures or blends of components having various particle sizes. Thus, for example, certain coal and coke products and industrial catalytic powders are sold having various particle sizes in specified ranges by weight. Crushed stone products that are used in the construction of roadways may also include mixtures or blends of several particle sizes in various specified ranges, depending on the anticipated use. Several such crushed stone products, as well as sand and/or other aggregates and other additives are combined in specific weight percentages in the manufacture or processing of bituminous paving mixtures.

Samples of these aggregate products may be taken at various stages during the processing or manufacturing thereof for analysis to insure that the proper particle sizes are being produced. Such samples may be taken from conveyors or other transport devices, or from product stockpiles, silos or other storage facilities. Such samples may be taken manually or automatically, and they may be taken from aggregate products produced by batch or continuous processes.

It is known, for example, that the particle size distribution in a quantity of aggregate materials may be determined more-or-less automatically. Thus, for example, U.S. Pat. No. 3,439,800 of Tonjes, U.S. Pat. No. 5,059,310 of Fischer et al. and U.S. Pat. No. 5,222,605 of Pogue describe methods and devices for automatically determining the proportionate amounts of various particle sizes of such a product. Such methods and devices are typically used to determine if a sample of an aggregate product meets required specifications for particle size distribution. However, it would be desirable if a sampling method and apparatus could be developed that could control the crushers or other equipment that is employed in processing or manufacturing the product. It would also be desirable if such a method and apparatus could be developed that would provide quicker and more accurate analysis of the gradation of a sample.

ADVANTAGES OF THE INVENTION

Among the advantages of the invention is that it provides a system that may be used in automatically controlling the processing or manufacturing of an aggregate product based upon the analysis of the particle size distribution of a sample of the product. Another advantage of the invention is that it includes a gradation assembly that may be vibrated in such a way as to provide a quick, accurate and efficient analysis of the particle size distribution of a sample.

Additional objects and advantages of this invention will become apparent from an examination of the drawings and the ensuing description.

EXPLANATION OF TECHNICAL TERMS

As used herein, aggregate materials refers to materials that are produced and/or sold in particulate form with or without other additives, such as, for example, crushed limestone and other types of crushed stone, bituminous paving mixtures such as hot-mix asphalt and cold mix, gravel, sand, lime, coal, coke, metallic oxide and other powders used for catalytic or other reactive purposes, and similar materials.

As used herein, a product which includes aggregate materials of various particle sizes in a predetermined weight ratio refers to a product comprised of one or more aggregate materials having a plurality of particle sizes in a predetermined ratio by weight.

SUMMARY OF THE INVENTION

The invention comprises a system for controlling the production of a product which includes aggregate materials of various particle sizes in a predetermined weight ratio. More specifically, the invention comprises a system for controlling the operation of an item of equipment, such as a crusher, for processing materials to produce such a product. The system includes a sampling device for obtaining a sample of the product from a predetermined location and a gradation assembly. The gradation assembly includes a plurality of gradation screens and a weighing pan that is adapted for measuring the weight of aggregate material. The gradation screens are supported by a frame in a generally horizontal attitude in a stacked arrangement, so that each screen in the stack has screen openings that are smaller than those of the screen immediately above it in the stack. The assembly also includes means for vibrating the screens and means for sequentially depositing the aggregate material that is retained on each screen or that passes through all of the screens in the weighing pan. Means are also provided for determining the ratios of the weights of the amounts of the aggregate materials that are retained on each of the screens or that passes through all of the screens to the total weight of the sample, and means for determining if each of the ratios of the weights of the amounts of the aggregate materials that are retained on each of the screens or that passes through all of the screens to the total weight of the sample meets a predetermined standard. The system also includes means for adjusting the operation of the item of equipment if the ratio of the weight of the aggregate materials that are retained on any of the screens or that passes through all of the screens to the total weight of the sample fails to meet the predetermined standard.

In order to facilitate an understanding of the invention, the preferred embodiments of the invention are illustrated in the drawings, and a detailed description thereof follows. It is not intended, however, that the invention be limited to the particular embodiments described or to use in connection with the apparatus illustrated herein. Various modifications and alternative embodiments such as would ordinarily occur to one skilled in the art to which the invention relates are also contemplated and included within the scope of the invention described and claimed herein.

BRIEF DESCRIPTION OF THE DRAWINGS

The presently preferred embodiments of the invention are illustrated in the accompanying drawings, in which like reference numerals represent like parts throughout, and in which.

DESCRIPTION OF THE PREFERRED EMBODIMENTS OF THE INVENTION

Figure 1:
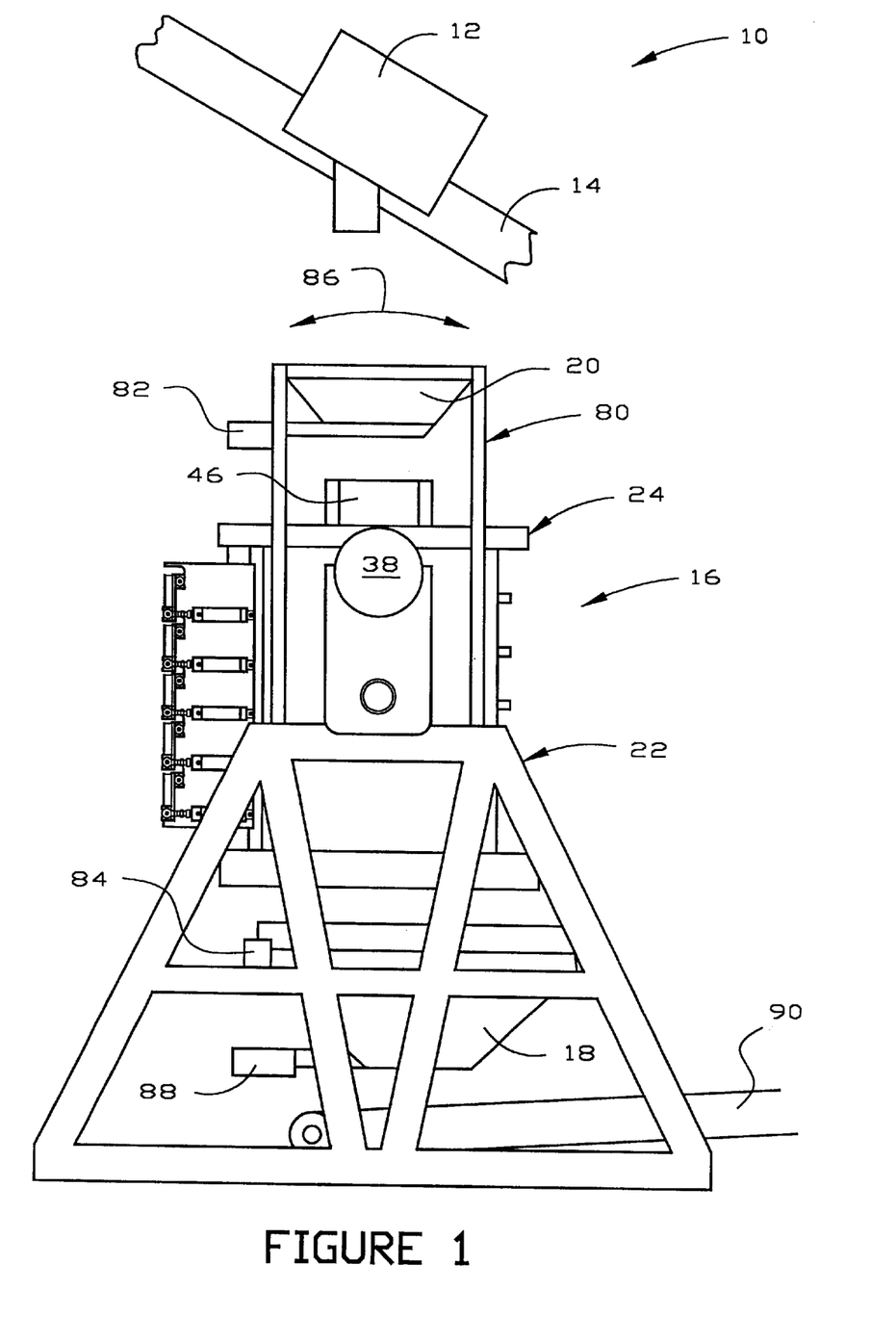
FIG. 1 is a side view of a portion of the apparatus of a preferred embodiment of the invention, showing the supporting frame for the gradation screens in a first position in which the screens are disposed generally horizontally in the stack.
Figure 8:
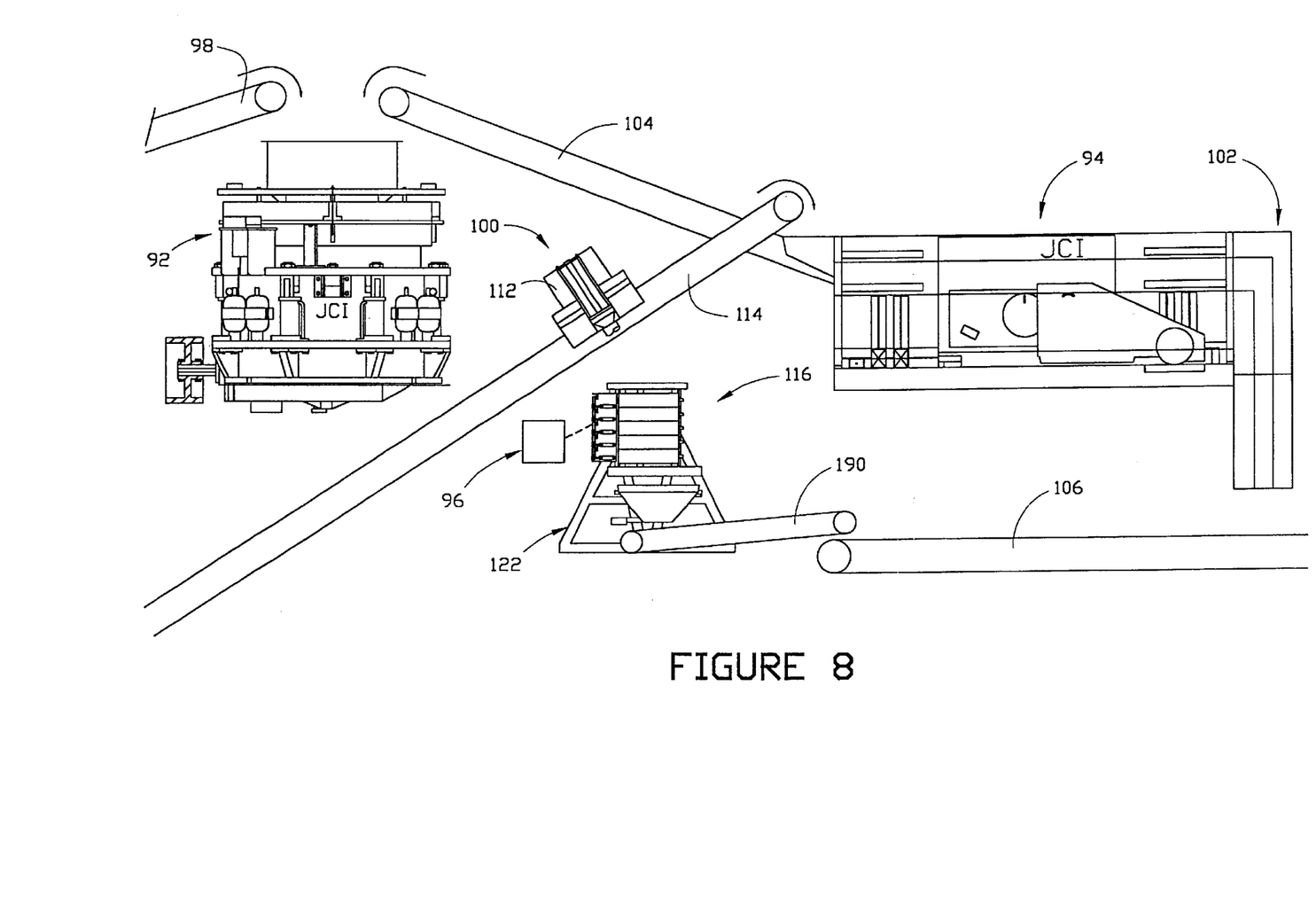
FIG. 8 is a plan view of an aggregate crushing and screening facility that may be controlled by operation of a preferred embodiment of the invention.

FIG. 1 illustrates system 10, comprising a portion of a preferred embodiment of an apparatus that may be utilized in controlling the production of a product which includes aggregate materials of various particle sizes in a predetermined weight ratio. The system controls such production by controlling the operation of an item of equipment for processing materials to produce such a product. The operation of a crusher and/or a vibratory screen assembly (and/or a blending chute associated therewith) in connection with an aggregate plant for producing crushed limestone or for producing or processing other aggregate products (including, for example, coal and coke) may be controlled by the system, and such a plant is illustrated in FIG. 8 (discussed hereinafter in more detail). The system may also be utilized to control the operation of other types of equipment as well, so long as such equipment is used in the production of a product which includes aggregate materials of various particle sizes in a predetermined weight ratio.

Preferred system 10 includes sampling device 12 for obtaining a sample of the product from a predetermined location, such as from conveyor 14. Such sampling devices are commercially available and are commonly used in connection with the sampling of stone or coal. Such devices are typically adapted to take a primary sample cut across the width of a conveyor at various timed intervals or on demand.

Figure 4:
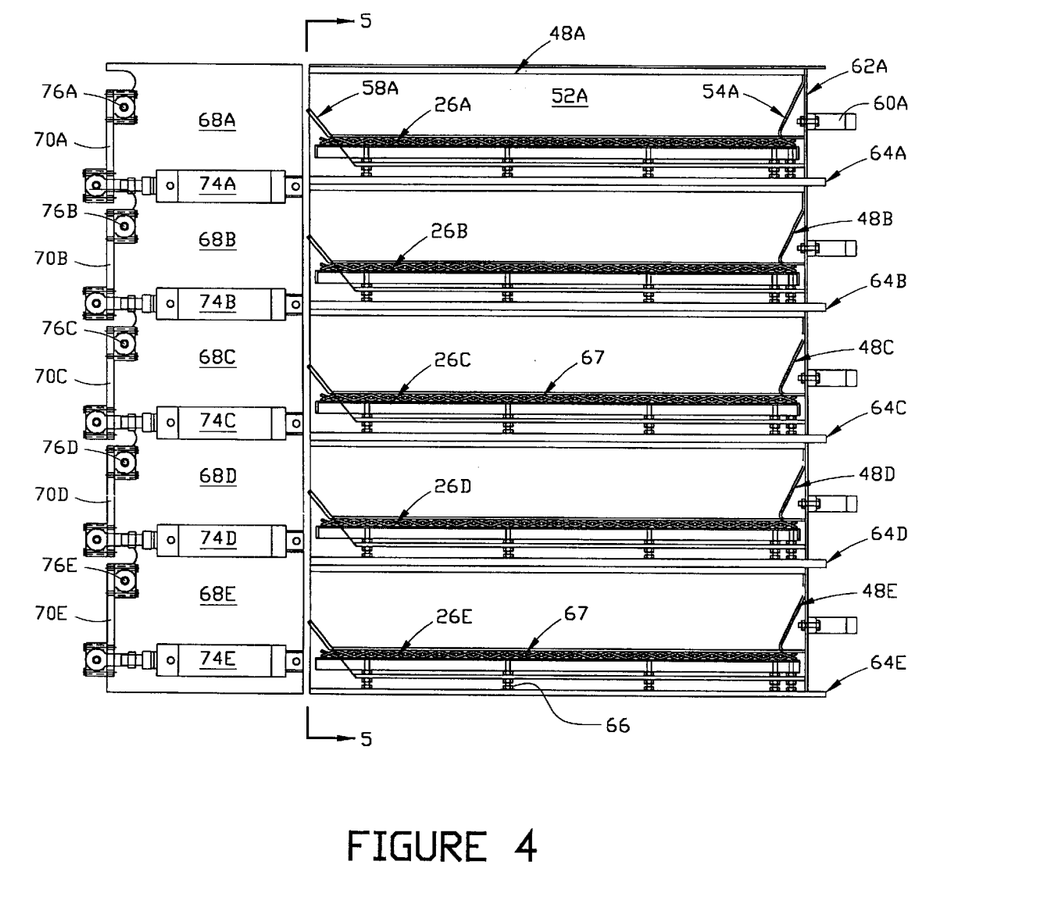
FIG. 4 is a side view of the screen assembly of the apparatus of FIG. 1, showing the screens and associated trays and chutes in a first position in which the screens are disposed generally horizontally in the stack.
Figure 5:
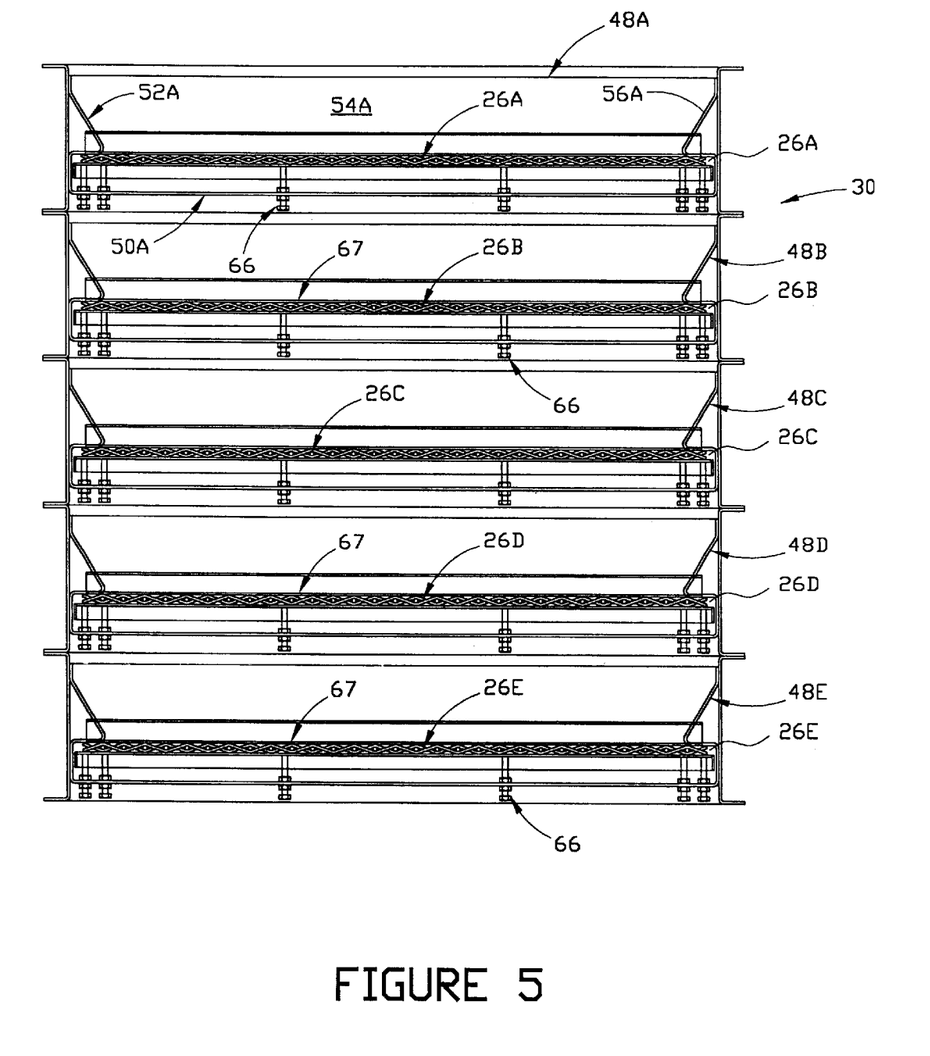
FIG. 5 is an end view of a portion of the screen assembly of the apparatus of FIG. 4, taken along the line 5—5 of FIG. 4.
Figure 6:
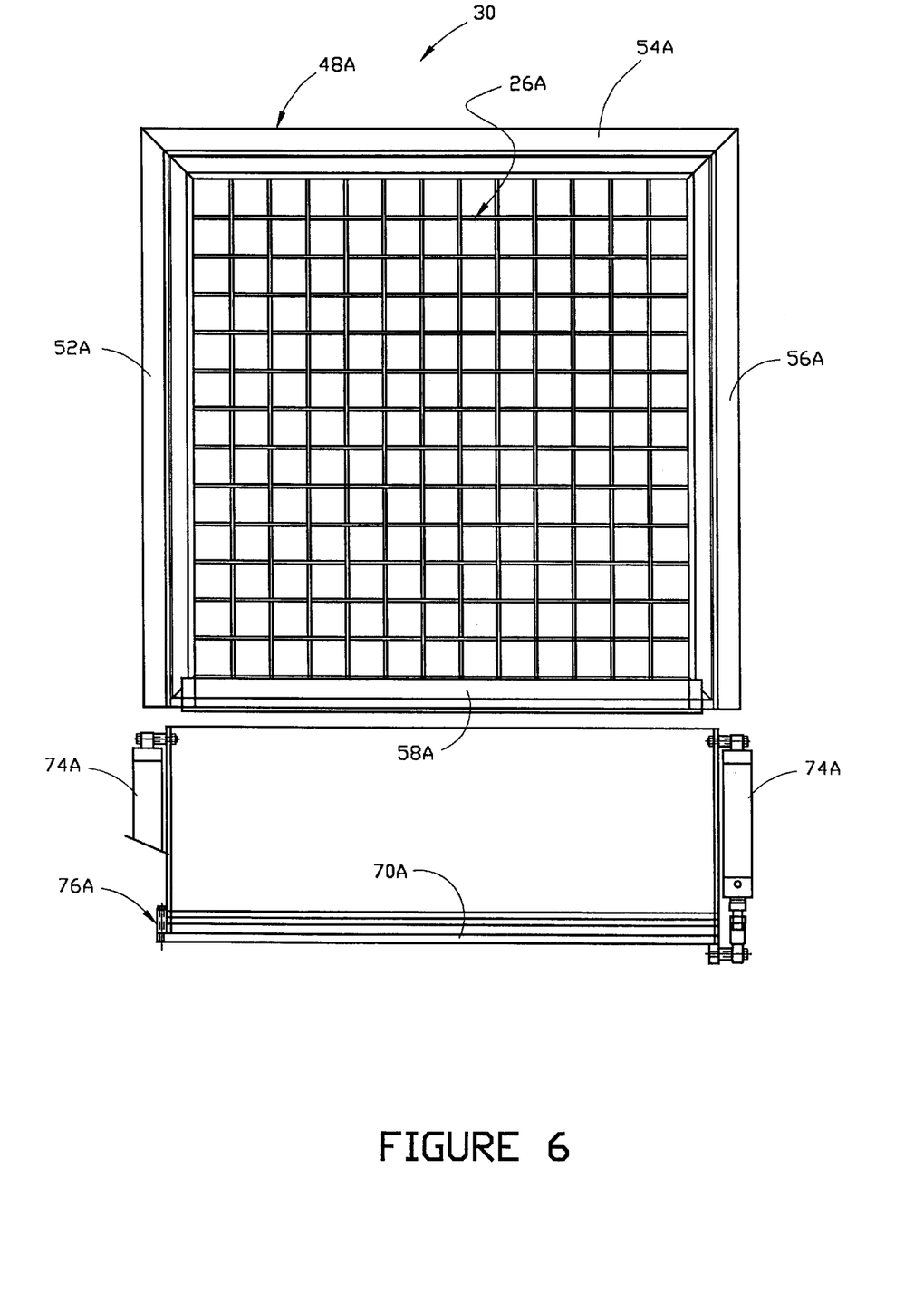
FIG. 6 is a top view of the apparatus of FIG. 4.

System 10 also includes gradation assembly 16, weighing pan 18 and metering hopper 20, all of which are mounted on support base 22. Although not required, the metering hopper may incorporate a drier to dry the aggregate, or a separate drier (not shown, and also not required) may be employed between the sampling device and the metering hopper. The gradation assembly includes a frame 24 which is adapted to support a plurality of gradation screens in a generally horizontal attitude (as shown in FIGS. 1, 4 and 5) in a stacked arrangement. The screens are arranged with the screen having the largest screen openings at the top of the stack and each of the other screens in the stack having screen openings that are smaller than those of the screen immediately above it in the stack. Various screen sizes may be utilized, depending on the desired particle sizes (or particle size ranges) of aggregate materials in the product. As shown in FIGS. 4–6, screens 26a, 26b, 26c, 26d and 26e are mounted in a stacked arrangement in the gradation assembly. Although five such screens are illustrated in the drawings, any number of screens greater than one may be employed in connection with the invention, depending primarily on the number of different particle sizes (or particle size ranges) of aggregate materials in the product.

Figure 2:
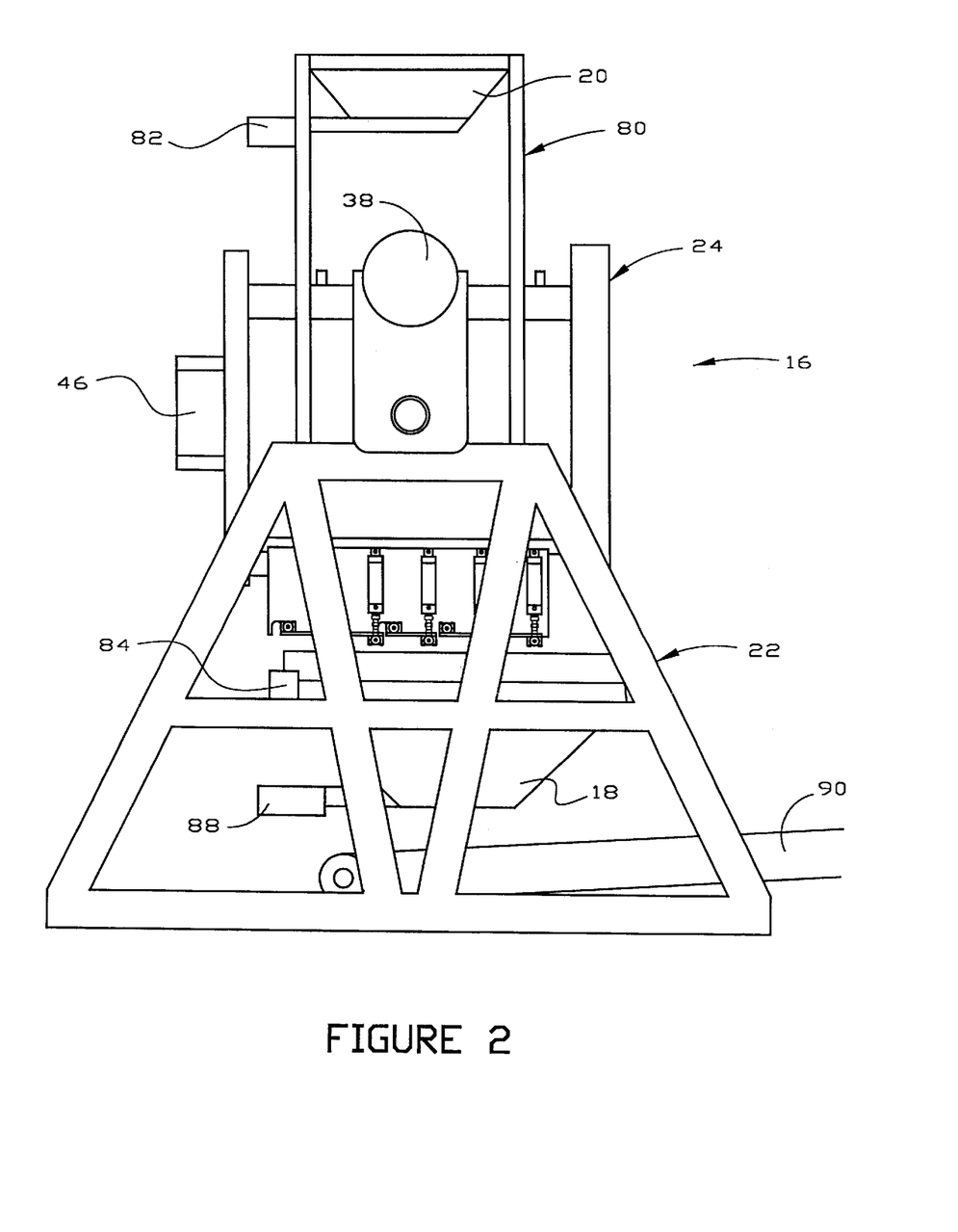
FIG. 2 is a side view of a portion of the apparatus of FIG. 1, showing the supporting frame for the gradation screens in a second position in which the screens are disposed generally vertically in the stack.
Figure 3:
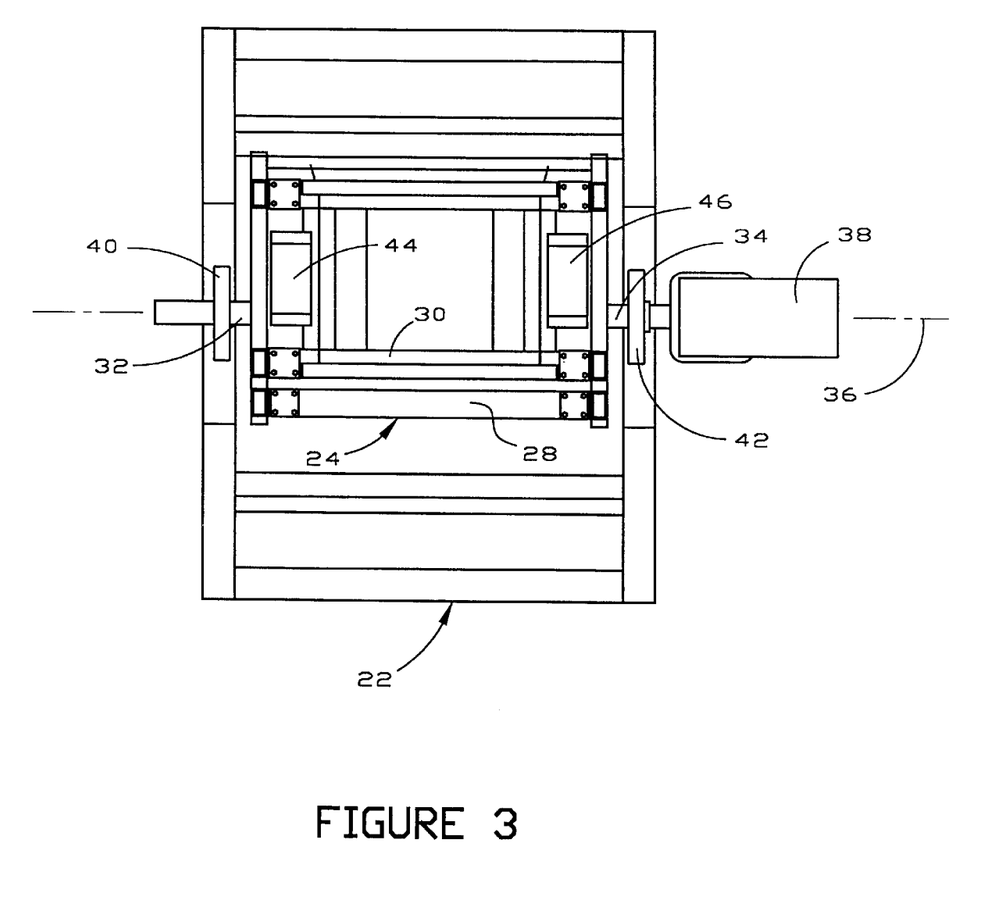
FIG. 3 is a top view of a portion of the apparatus of FIG. 2, with the metering hopper, weighing pan, screens and associated components deleted.

Preferably, frame 24 is comprised of an outer frame portion 28 and an inner frame portion 30 (best shown in FIG. 3) in which the gradation screens are mounted. Frame 24 is rotatable from a first frame position (illustrated in FIG. 1), in which the screens are disposed in a generally horizontal attitude, to a second frame position (shown in FIG. 2), in which the screens are disposed generally vertically. Although it is preferred that the screens in the first position be oriented precisely horizontally with respect to the ground, any angle of orientation that will permit the passage of material that is smaller than the openings in a screen through such screen to the screen below it in the stack may be encompassed by the term "generally horizontal". Furthermore, it is not necessary that all of the screens be oriented at precisely the same "generally horizontal" attitude, so long as the condition described above is met with respect to each screen in the stack. Finally, although it is preferred that the screens in the second position be oriented precisely vertically with respect to the ground, any angle of orientation that will facilitate the discharge of material that is retained on the screens into the associated chutes (as subsequently described in more detail) may be encompassed by the term "generally vertically", and it is not necessary that all of the screens be oriented at precisely the same "generally vertical" attitude, so long as the condition described above is met with respect to each screen in the stack.

A pair of stub shafts 32 and 34 define an axis of rotation 36 (see FIG. 3) about which support frame 24 is rotated by operation of gearmotor 38. Preferably, axis 36 intersects the center of mass of frame 24 and its components. One end of each of the stub shafts is preferably welded to the side of outer frame portion 28 of support frame 24, and the shafts are adapted for rotation in pillow block bearings 40 and 42 which are bolted or otherwise attached to base 22. The gearmotor (or shaft 34) is preferably fitted with a brake to permit locking of support frame 24 in either the first frame position, in which the screens are disposed generally horizontally, or the second frame position, in which the screens are disposed generally vertically. A pair of vibrating motors 44 and 46 comprising motors having eccentrically mounted weights on a rotating shaft, or other vibrating means, are mounted on inner frame portion 30. The outer frame portion 28 is preferably isolated from the vibrations imposed on inner frame portion 30 by a plurality of rubber cushions or other elastomeric isolators (not shown).

Referring now to FIGS. 4–6, preferred inner frame portion 30 includes a plurality of trays in which the screens are mounted in a stacked arrangement. Thus, screen 26a is mounted in tray 48a at the top of the stacked arrangement when the screens are in the first (generally horizontal) screen position. Similarly, screen 26b is mounted in tray 48b just beneath screen 26a, screen 26c is mounted in tray 48c just beneath screen 26b, screen 26d is mounted in tray 48d just beneath screen 26c and screen 26e is mounted in tray 48e just beneath screen 26d. In the alternative, tray 48e and screen 26e may be replaced by a tray having a solid floor (not shown) that is adapted to collect fine material that passes through all of the screens.

Each tray of the preferred embodiment of the invention is essentially identical to each other tray, as shown in FIGS. 4–6. Thus, for example, tray 48a is comprised of peripheral floor 50a, three aggregate retaining walls 52a, 54a and 56a, and an aggregate releasing wall 58a, as shown in FIGS. 4 and 5. The peripheral floor of each tray supports the peripheral edges of its associated screen, leaving the area beneath the screen cloth of the screen open to permit aggregate material that is small enough to pass through the openings in the screen cloth to drop down to the screen below (when the screens are in the first position). The shape of the tray and the height of its aggregate retaining and aggregate releasing walls are preferably such that aggregate that is too large to pass through the screen mounted therein will be retained within the tray while the screen is being vibrated in the first position. The aggregate releasing wall is preferably sized so that upon rotation of the screen to the second position, aggregate retained on the screen may pass over the aggregate retaining wall and into the associated chute (as hereinafter described).

Figure 7:
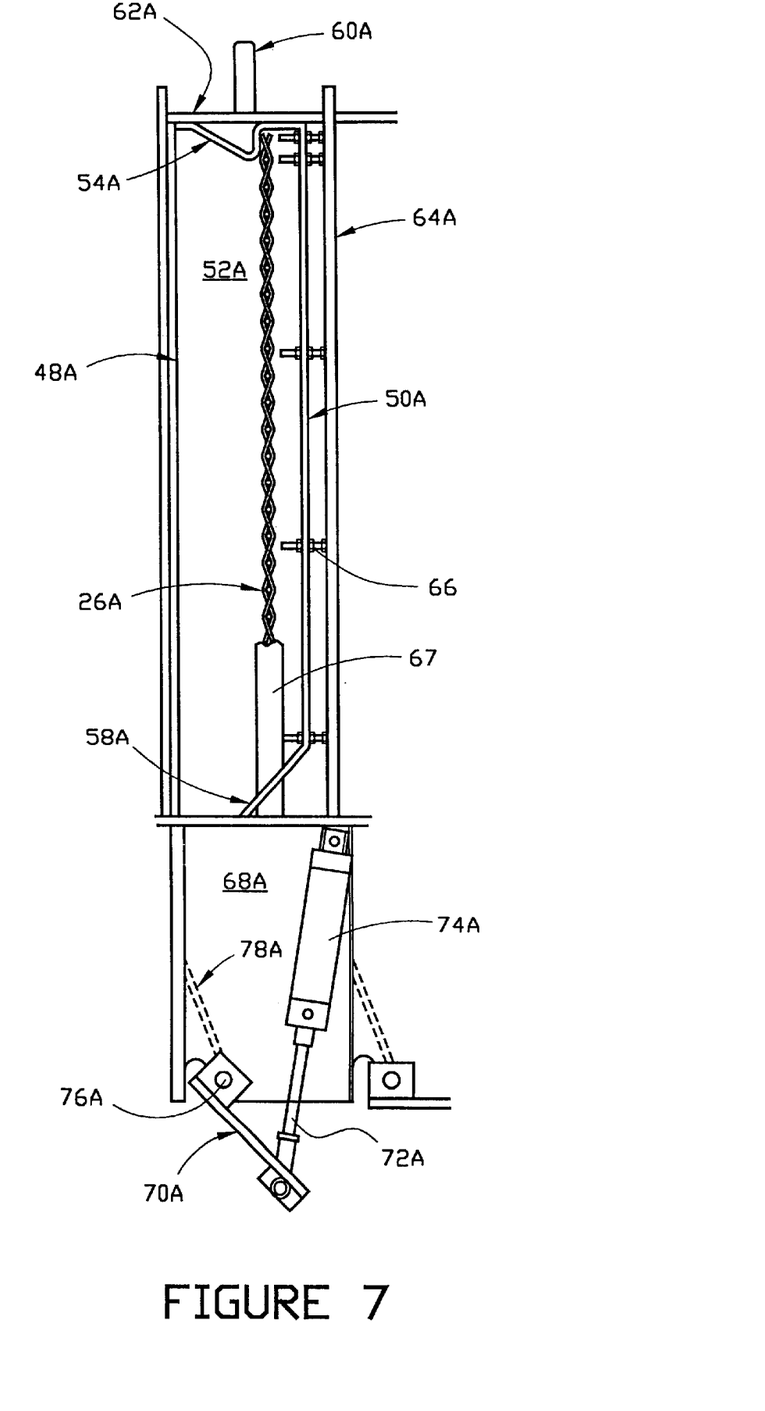
FIG. 7 is a side view of a portion of the screen assembly of FIG. 4, showing a screen and associated tray and chute in a second position in which the screen is disposed generally vertically in the stack, and showing the chute door in an open position.

Access handle 60a (see FIG. 4) is attached to end wall 62a which is located adjacent to aggregate retaining wall 54a and opposite aggregate releasing wall 58a. Similar access handles are attached to trays 26b, 26c, 26d, and 26e. Trays 26a, 26b, 26c, 26d and 26e are supported on peripheral dividers 64a, 64b, 64c, 64d and 64e respectively, which are disposed around the periphery of inner frame portion 30, and bolts 66 are provided to hold the screens securely in place in the trays. Preferably, as shown in FIGS. 4, 5 and 7, the outer peripheries of the screens are bounded by angles 67, and bolts 66 bear against the bottom of the angles to hold the screens securely in place. When it is desired to remove a tray to replace a screen or for another reason, the handle may be grasped and the tray pulled out of the inner frame portion to the right as viewed in FIG. 4.

A chute is provided for each tray and screen assembly in inner frame portion 30 of preferred assembly 10. Thus, as shown in FIG. 4, chute 68a is provided for tray 48a and its associated screen, chute 68b is provided for tray 48b and its associated screen, chute 68c is provided for tray 48c and its associated screen, chute 68d is provided for tray 48d and its associated screen, and chute 68e is provided for tray 48e and its associated screen (or for an alternative tray having a solid floor). Each chute has a door at its end which is pivotally mounted so as to swing open upon extension of a pair of cylinders that are mounted at either side thereof so that material in the chute may be discharged from the chute when frame 24 is in the second position with the screens disposed generally vertically. Such cylinders may be fluid powered, such as, for example air cylinders. FIG. 7 illustrates the relationship of chute 68a, tray 48a and screen 26a when screen 26a is disposed in the generally vertical (or second) position. As shown therein, chute 68a is provided with door 70a which is actuated by the extension of a pair of pistons 72a (only one of which is shown) from cylinders 74a (see FIG. 6) to pivot open about pivot axis 76a. It is preferred that an inner angled wall 78a be provided within chute 68a to divert material discharged from the chute away from the pivoting hinge (or axis 76a) of door 70a. Chutes 68b, 68c, 68d and 68e are essentially identical to chute 68a. Door 70b of chute 68b may be pivoted about pivot axis 76b to open upon actuation of cylinders 74b (only one of which is shown). Similarly, doors 70c, 70d and 70e of chutes 68c, 68d and 68e respectively may be pivoted about pivot axes 76c, 76d and 76e respectively to open upon actuation of cylinder pairs 74c, 74d and 74e (only one of each pair of which is shown in the drawings). When the screen assembly is rotated to the second position, any material that is retained on a screen (or any material that is retained in a solid floor tray that is substituted for tray 48e and screen 26e) will fall past the aggregate releasing wall of its tray and into its associated chute for subsequent discharge through the chute door.

Referring again to FIG. 1, system 10 is preferably controlled by a computer (not shown in FIG. 1) and connected to existing control systems on a crusher or other item of equipment. The software utilized by the computer is readily available for industrial control applications. Such software is capable of computing percentage data, compiling statistical data and maintaining historical data. The software should also be capable of implementing timed automatic sampling, automated random sampling and operator override control sampling. In a preferred embodiment of the invention, the system is connected to control means for the item of equipment for adjusting the maximum particle size of the product that may be produced thereby. The use of a computer and available industrial control software, and the connection of the system to control systems for crushers or other items of equipment would be within the knowledge of those having ordinary skill in the art to which the invention relates.

To begin operation of the system, frame 24 is placed in a first frame position that is adapted to support the gradation screens in a generally horizontal attitude. A signal from the computer controller or other starting device will actuate sampling device 12 to take a sample from conveyor 14 and deposit it in metering hopper 20, which is mounted on support base 22 by hopper frame 80. Samples may be taken at any convenient interval and in any convenient size. Typically, a sample comprising 10 to 100 pounds will be taken as often as every ten minutes or as infrequently as once per hour when the system is used to control a rock crusher.

The metering hopper is preferably fitted with cylinder 82 which slowly opens a gate (not shown) in the bottom of the hopper, allowing the sample to drop onto screen 26a at a controlled rate. Preferably, the metering hopper will deposit the sample on the uppermost screen in the stack at a rate within the range of about 40% to about 80% by weight of the total sample per minute.

Prior to deposit of the sample onto screen 26a (or prior to deposit of any portion of the sample into weighing pan 18, if tray 48e and screen 26e have been replaced by a tray having a solid floor that is adapted to collect fine material that passes through all of the screens), one or more load cells 84 (only one of which is shown) on weighing pan 18 will weigh the pan to obtain a tare (or empty weight). This weight will be recorded and saved by software associated with the controlling computer.

As cylinder 82 is actuated to deposit the sample on the first screen of the gradation assembly, vibrator motors 44 and 46 or other vibrating means are actuated to vibrate the screens in the gradation assembly. Preferably, the vibration is confined to inner frame portion 30 of frame 24 by suitable elastomeric isolators (not shown). The screens may be vibrated in the first position for any suitable length of time. When used to control the operation of a rock crusher, the screen assembly is preferably vibrated in the first position for about 50 to about 125 seconds, most preferably for about 90 seconds. Preferably, the vibrating motors are adapted to apply vibrations to the screens in a series of frequencies, with the first frequency being adapted to induce resonance in the uppermost screen in the stack and each subsequent frequency being adapted to induce resonance in a screen immediately below the screen in which resonance was previously induced. Thus, as illustrated in the drawings, vibrating motors 44 and 46 will preferably apply vibrations to the gradation assembly at a first frequency adapted to induce resonance in screen 26a for about 10 to about 25 seconds, most preferably for about 18 seconds. Then the vibrating motors will change the frequency at which vibrations are applied to a second frequency that is adapted to induce resonance in screen 26b for a period of time similar to that at which vibrations were applied at the resonance frequency of screen 26a. Then the vibrating motors will change the frequency at which vibrations are applied to a third frequency that is adapted to induce resonance in screen 26c for a period of time similar to that at which vibrations were applied at the resonance frequencies of screens 26a and 26b. Then the vibrating motors will change the frequency at which vibrations are applied to a fourth frequency that is adapted to induce resonance in screen 26d for a period of time similar to that at which vibrations were applied at the resonance frequencies of screens 26a, 26b and 26c. Finally, the vibrating motors will change the frequency at which vibrations are applied to a fifth frequency that is adapted to induce resonance in screen 26e for a period of time similar to that at which vibrations were applied at the resonance frequencies of screens 26a, 26b, 26c and 26d. Of course, depending on the nature of the aggregate product that is being sampled, it may be desirable to vibrate certain screens at their resonance frequencies for a period of time that is different from that at which certain other screens are vibrated at their resonance frequencies.

It is also preferred that during vibration of the screens in the first position, the gearmotor be actuated to rotate shaft 34 first in one direction and then the other in order to rock frame 24 back and forth about pivot axis 36 through an angular displacement, preferably within the range of less than about 20°, as illustrated by arrow 86 of FIG. 1. As the screens are vibrated, aggregate material that is small enough to pass through the openings in the screen cloth at each screen level will pass through and be screened through lower screens in the stack. Material that passes through all five screens (or such other number as may be employed) will fall into weighing pan 18 (or be retained in a solid-floored tray that is substituted for tray 48e and screen 26e). When vibration in the first frame position has been completed, cylinder 82 will be actuated to close the gate in metering hopper 20 and gearmotor 38 will be actuated to rotate frame 24 from the first position to a second position in which the screens are disposed generally vertically. As frame 24 is rotated to the second position, aggregate material retained on each of the screens (or on a solid-floored tray that is substituted for the lowermost screen) will fall into the chutes associated with the screens. Preferably, the vibrating motors will be actuated (or will continue to operate) to vibrate the screens while the frame is in the second frame position in order to dislodge any material that is caught in the screens. The screens may be vibrated in the second position for any suitable length of time. When used to control the operation of a rock crusher, the screen assembly is preferably vibrated in the second position for about 10 to about 60 seconds, most preferably for about 30 seconds. Preferably, the vibrating motors are adapted to apply vibrations to the screens in a series of frequencies, with each such frequency being adapted to induce resonance in one of the screens in the stack. Thus, for example, vibrating motors 44 and 46 may be operated to apply vibrations to the gradation assembly at a first frequency adapted to induce resonance in screen 26a for about 5 to about 10 seconds, most preferably for about 8 seconds. Then the frequency at which vibrations are applied may be changed to a second frequency that is adapted to induce resonance in screen 26b for a period of time similar to that at which vibrations were applied at the resonance frequency of screen 26a. Then the frequency at which vibrations are applied may be changed to a third frequency that is adapted to induce resonance in screen 26c for a period of time similar to that at which vibrations were applied at the resonance frequencies of screens 26a and 26b. Then the frequency at which vibrations are applied may be changed to a fourth frequency that is adapted to induce resonance in screen 26d for a period of time similar to that at which vibrations were applied at the resonance frequencies of screens 26a, 26b and 26c. Finally, the frequency at which vibrations are applied may be changed to a fifth frequency that is adapted to induce resonance in screen 26e for a period of time similar to that at which vibrations were applied at the resonance frequencies of screens 26a, 26b, 26c and 26d. Although the application of vibrations at the resonance frequencies of the various screens in the second position has been described herein in a particular sequence, such vibrations may be applied to the various screens in any order or sequence according to this preferred embodiment of the invention.

After completing vibration of the screens at the second position, the vibrating motors will be shut off, and one or more load cells 84 on weighing pan 18 will weigh the contents of the material in the weighing pan that has passed through all of the screens (unless a solid-floored tray has been substituted for tray 48e and screen 26e). This weight will be recorded and saved by software associated with the controlling computer. Subsequently, cylinders 74a are actuated to open chute door 70a to permit the contents of chute 68a to fall into weighing pan 18. The amount deposited in the pan will be weighed and this weight will be recorded and saved. If material has been previously weighed in the weighing pan, the difference between the previously recorded weight (less the tare weight) immediately prior to discharge of material from chute 68a and the weight (less the tare weight) with the material from chute 68a will be calculated to determine the weight of the material retained on screen 26a and discharged into the weighing pan through chute 68a. Chute door 70a will then be closed by retraction of the pistons of cylinders 74a, and chute door 70b will be opened to permit the contents of chute 68b to fall into weighing pan 18. The amount deposited in the pan will be weighed and this weight will be recorded and saved. The difference between the previously recorded weight (less the tare weight) immediately prior to discharge of material from chute 68b and the weight (less the tare weight) with the material from chute 68b will be calculated to determine the weight of the material retained on screen 26b and discharged into the weighing pan through chute 68b. Chute door 70b will then be closed by retraction of the pistons of cylinders 74b, and chute door 70c will be opened to permit the contents of chute 68c to fall into weighing pan 18. The amount deposited in the pan will be weighed and this weight will be recorded and saved. The difference between the previously recorded weight (less the tare weight) immediately prior to discharge of material from chute 68c and the weight (less the tare weight) with the material from chute 68c will be calculated to determine the weight of the material retained on screen 26c and discharged into the weighing pan through chute 68*c*. Chute door 70*c* will then be closed by retraction of the pistons of cylinders 74*c*, and chute door 70*d* will be opened to permit the contents of chute 68*d* to fall into weighing pan 18. The amount deposited in the pan will be weighed and this weight will be recorded and saved. The difference between the previously recorded weight (less the tare weight) immediately prior to discharge of material from chute 68*d* and the weight (less the tare weight) with the material from chute 68*d* will be calculated to determine the weight of the material retained on screen 26*d* and discharged into the weighing pan through chute 68*d*. Chute door 70*d* will then be closed by retraction of the pistons of cylinders 74*d*, and chute door 70*e* will be opened to permit the contents of chute 68*e* to fall into weighing pan 18. The amount deposited in the pan will be weighed and this weight will be recorded and saved. The difference between the previously recorded weight (less the tare weight) immediately prior to discharge of material from chute 68*e* and the weight (less the tare weight) with the material from chute 68*e* will be calculated to determine the weight of the material retained on screen 26*e* (or retained by a solid-floor tray that has been substituted for tray 48*e* and screen 26*e*) and discharged into the weighing pan through chute 68*e*. Chute door 70*e* will then be closed by retraction of the pistons of cylinders 74*e*.

The order in which the chute doors are opened so that material contained therein may be deposited in the weighing pan is not particularly critical, so long as the system operates to sequentially deposit the aggregate material that is retained on each screen in the weighing pan. After all of the material in the sample has been weighed, the preferred system's computer will determine the total weight of the sample (by adding all of the amounts that are retained on each of the screens and the amount which passes through all of the screens). The computer will then determine the ratios of the weights of the amounts of the aggregate materials that are retained on each of the screens (or which passes through all of the screens) to the total weight of the sample. A predetermined standard for each such ratio will have been stored in the computer, and the computer will then compare each calculated ratio (of the weight of material retained on a screen or passing through all of the screens) to the predetermined standard for such sized material. If the computer determines that any ratio of the weight of the amount of the aggregate materials that is retained on any of the screens (or which passes through all of the screens) to the total weight of the sample fails to meet the predetermined standard for such screen size, it will adjust the existing control systems on the crusher or other item of equipment to change the operation of the equipment to bring the weight of the materials retained on the screens (or which passes through all of the screens) within applicable weight ratio standards. In a preferred embodiment of the invention, the system is connected to control means for adjusting the maximum particle size of the product that may be produced by a crusher. In an alternative embodiment of the invention, the system, with appropriate software adjustment, may be operated to bypass any given tray position for chute discharge, or to determine one or more ratios based upon a combination of the material discharged through two or more chutes.

After all weight calculations have been made, weighing pan cylinder 88 may be actuated to open a gate (not shown) in the weighing pan to drop the material therein onto return conveyor 90. The gate is then closed and frame 24 is rotated to the first frame position. As has been mentioned, the invention is particularly adapted for use in controlling the operation of a crusher and/or a vibratory screen assembly.

Thus as shown in FIG. 8, system 100, which is comparable to system 10 and comprised of sampling device 112 (comparable to sampling device 12), gradation assembly 116 (comparable to gradation assembly 16), a weighing pan (not shown but comparable to weighing pan 18) and a metering hopper (also not shown but comparable to metering hopper 20), all of which are mounted on support base 122 (comparable to support base 22), may be utilized to control an aggregate processing facility comprising crusher 92 and/or vibratory screen assembly 94. System 100 is preferably controlled by a computer such as programmable logic controller 96 which is connected to system 100 and to the existing control systems on crusher 92 and/or vibratory screen assembly 94 by conventional wiring, fiber optic cable, radio transmitter or other known means (not shown). Preferably crusher 92 is a cone crusher such as is described in U.S. Pat. No. 5,950,939 and U.S. Pat. No. 6,032,886, the disclosures of which are incorporated herein by reference, although the invention is adapted for use on controlling other types of crushers including vertical and horizontal impactors. Screening assembly 94 is a conventional vibratory screen that is provided with an adjustable blending chute 102, which may be used to blend material retained on two or more screens and/or to channel such material, or material retained on a single (usually the top) screen, to conveyor 104 for return to the crusher. The crusher may be provided with a variable speed motor, and if so, system 100 may be operated to control the operating speed of the crusher. In addition, the system may be operated to control the hydraulic motors which regulate the closed side setting of the crusher. The system may also control the discharge gates of blending chute 102 which control the blending of material retained on the various screens of screen assembly 94 and/or the return of at least a portion of such material to the crusher. Aggregate material to be processed is fed into the top of crusher 92 by conveyor 98. Such material is crushed in the crusher and discharged from the bottom thereof onto conveyor 114 (comparable to conveyor 14 of FIG. 1). Material from conveyor 114 is fed into the top of vibratory screen assembly 94. Material that is too large to pass through the uppermost screen of assembly 94 is returned to the crusher by operation of blending chute 102 via conveyor 104. Material that is retained on the other screens (or which passes through the screens) of assembly 94 may be blended by the blending chute and/or discharged onto conveyors 104 and 106.

Sampling device 1 12 is adapted to take a representative sample of the material on conveyor 114 and discharge it into the metering hopper (not shown) of system 100. After system 100 has graded the material obtained from conveyor 114 and all weight calculations have been made, the weighing pan cylinder (not shown) may be actuated to open a gate (not shown) in the weighing pan to drop the material therein onto return conveyor 190. Material on the return conveyor is transported to conveyor 106 or to another conveyor (not shown).

Although this description contains many specifics, these should not be construed as limiting the scope of the invention but as merely providing illustrations of some of the presently preferred embodiments thereof, as well as the best mode contemplated by the inventors of carrying out the invention. The invention, as described herein, is susceptible to various modifications and adaptations, and the same are intended to be comprehended within the meaning and range of equivalents of the appended claims.

What is claimed is:

1. A system for controlling the operation of an item of equipment for processing materials to produce a product which includes aggregate materials of various particle sizes in a predetermined weight ratio, said system comprising:
(A) a sampling device for obtaining a sample of the product from a predetermined location;
(B) a gradation assembly comprising:
  (1) a base;
  (2) a plurality of gradation screens;
  (3) a frame that is rotatably mounted on the base and adapted to support the gradation screens in a first frame position in which the screens are disposed in a generally horizontal attitude in a stacked arrangement whereby each screen in the stack has screen openings that are smaller than those of the screen immediately above it in the stack, and in a second frame position in which the screens are disposed generally vertically;
  (4) means for vibrating the screens while the frame is in the first frame position;
(C) a weighing pan that is adapted for measuring the weight of aggregate material;
(D) means for rotating the frame from the first frame position to the second frame position;
(E) means for sequentially depositing the aggregate material that is retained on each screen, or that passes through all of the screens, in the weighing pan;
(F) means for determining the ratios of the weights of the amounts of the aggregate materials that are retained on each of the screens or that passes through all of the screens to the total weight of the sample;
(G) means for determining if each of the ratios of the weights of the amounts of the aggregate materials that are retained on each of the screens or that passes through all of the screens to the total weight of the sample meets a predetermined standard;
(H) means for adjusting the operation of the item of equipment if the ratio of the weight of the aggregate materials that are retained on any of the screens or that passes through all of the screens to the total weight of the sample fails to meet the predetermined standard.

2. The system of claim 1 wherein the means for vibrating the screens applies vibrations in a series of frequencies, with said first frequency being applied to induce resonance in the uppermost screen in the stack and each subsequent frequency being applied to induce resonance in a screen immediately below the screen in which resonance was previously induced.

3. The system of claim 1 wherein said system includes means for rocking said frame through an angular displacement of less than about 20° during vibration.

4. The system of claim 1 wherein the means for adjusting the operation of the item of equipment includes means for adjusting the maximum particle size of the product that may be produced thereby.

5. The system of claim 1 which includes a metering hopper for receiving the sample of the product from the sampling device and depositing the sample on the uppermost screen in the stack at a controlled rate.

6. The system of claim 5 wherein the metering hopper is adapted to deposit the sample on the uppermost screen in the stack at a rate of about 40% to about 80% by weight of the total sample per minute.

7. The system of claim 1 which includes means for vibrating the screens while the frame is in the second frame position by applying vibrations at a predetermined resonance frequency to each of the screens, with each such frequency being applied to induce resonance in one of the screens.

8. A system for controlling the operation of a crusher for production of aggregate materials having particle sizes in a predetermined weight ratio, said system comprising:
(A) a sampling device for obtaining a sample of the aggregate materials from a predetermined location on a product conveyor;
(B) a gradation assembly comprising:
  (1) a base;
  (2) a plurality of gradation screens;
  (3) a frame that is rotatably mounted on the base and adapted to support the gradation screens in a first frame position in which the screens are disposed in a generally horizontal attitude in a stacked arrangement whereby each screen in the stack has screen openings that are smaller than those of the screen immediately above it in the stack, and in a second frame position in which the screens are disposed generally vertically;
  (3) means for vibrating the screens while the frame is in the first frame position;
(C) a weighing pan that is adapted for measuring the weight of aggregate material;
(D) means for rotating the frame from the first frame position to the second frame position;
(E) means for sequentially depositing the aggregate material that is retained on each screen or that passes through all of the screens in the weighing pan;
(F) means for determining the ratios of the weights of the amounts of the aggregate materials that are retained on each of the screens or that passes through all of the screens to the total weight of the sample;
(G) means for determining if each of the ratios of the weights of the amounts of the aggregate materials that are retained on each of the screens or that passes through all of the screens to the total weight of the sample meets a predetermined standard;
(H) means for adjusting the operation of the crusher if the ratio of the weight of the aggregate materials that are retained on any of the screens or that passes through all of the screens to the total weight of the sample fails to meet the predetermined standard;
(I) means for depositing the sample of aggregate materials on a product conveyor.

9. The system of claim 8 wherein the means for vibrating the screens applies vibrations in a series of frequencies, with said first frequency being applied to induce resonance in the uppermost screen in the stack and each subsequent frequency being applied to induce resonance in a screen immediately below the screen in which resonance was previously induced.

10. The system of claim 8 which includes a motor mounted on the base, which motor is operatively connected to the frame and adapted for:
(a) rocking the frame through an angular displacement of less than about 20° while said frame is in the first frame position and during vibration; and
(b) rotating the frame from the first frame position to the second frame position.

11. The system of claim 8 which includes means for vibrating the screens while the frame is in the second frame position.

12. The system of claim 8 which includes a metering hopper for receiving the sample of the aggregate materials from the sampling device and depositing the sample on the uppermost screen in the stack at a controlled rate.

13. The system of claim 12 wherein the metering hopper is adapted to deposit the sample on the uppermost screen in the stack at a rate of about 40% to about 80% by weight of the total sample per minute.

14. A method for controlling the operation of a crusher for production of aggregate materials of various particle sizes in a predetermined weight ratio, said method comprising:

(A) providing a system comprising:
   (1) a sampling device for obtaining a sample of the product from a predetermined location;
   (2) a gradation assembly comprising:
      (a) a plurality of gradation screens, including a first screen, a second screen and a third screen;
      (b) a frame that is adapted to support the gradation screens in a first frame position in which the screens are disposed in a generally horizontal attitude in a stacked arrangement whereby each screen in the stack has screen openings that are smaller than those of the screen immediately above it in the stack, and in a second frame position in which the screens are disposed generally vertically;
      (c) means for vibrating the screens;
   (3) a weighing pan that is positioned beneath the gradation screens and which is adapted for measuring the weight of aggregate material;
   (4) means for moving the frame from the first frame position to the second frame position;
   (5) means for sequentially depositing the aggregate material that is retained on each screen or that passes through all of the screens in the weighing pan;
   (6) means for determining the ratios of the weights of the amounts of the aggregate materials that are retained on each of the screens or that passes through all of the screens to the total weight of the sample;
   (7) means for determining if each of the ratios of the weights of the amounts of the aggregate materials that are retained on each of the screens or that passes through all of the screens to the total weight of the sample meets a predetermined standard;
   (8) means for adjusting the operation of the crusher if the ratio of the weight of the aggregate materials that are retained on any of the screens or that passes through all of the screens to the total weight of the sample fails to meet the predetermined standard;

(B) obtaining a sample of the product;
(C) depositing the sample on the first screen of the gradation assembly while the frame is in the first frame position;
(D) vibrating the screens while the frame is in the first frame position;
(E) moving the frame from the first frame position to the second frame position;
(F) depositing the aggregate material that is retained on the first screen in the weighing pan;
(G) weighing the aggregate material that is in the weighing pan after step (F);
(H) depositing the aggregate material that is retained on the second screen in the weighing pan;
(I) weighing the aggregate material that is in the weighing pan after step (H);
(J) depositing the aggregate material that is retained on the third screen in the weighing pan;
(K) weighing the aggregate material that is in the weighing pan after step (J);
(L) calculating the ratio of the weight of the material that was deposited in the weighing pan in step (F) to the weight of the material that was weighed in step (K);
(M) calculating the ratio of the weight of the material that was deposited in the weighing pan in step (H) to the weight of the material that was weighed in step (K);
(N) calculating the ratio of the weight of the material that was deposited in the weighing pan in step (J) to the weight of the material that was weighed in step (K);
(O) determining if the weight ratio calculated in step (L) meets a first predetermined standard;
(P) determining if the weight ratio calculated in step (M) meets a second predetermined standard;
(Q) determining if the weight ratio calculated in step (N) meets a third predetermined standard;
(R) adjusting the operation of the crusher if one or more of the weight ratios calculated in steps (L), (M) and (N) fails to meet the corresponding predetermined standard.

15. The method of claim 14 wherein the screens are vibrated by applying vibrations in a series of frequencies, one for each screen, with said first frequency being applied to induce resonance in the first screen in the stack and each subsequent frequency being applied to induce resonance in a screen immediately below the screen in which resonance was previously induced.

16. The method of claim 14, which includes:
(A) providing a system which includes:
   (9) means for rocking said frame through an angular displacement of less than about 20° while said frame is in the first frame position during vibration;
(D) vibrating the screens while the frame is in the first frame position while rocking said frame through an angular displacement of less than about 20°.

17. The method of claim 14 which includes:
(A) providing a system which includes:
   (10) a metering hopper for receiving the sample of the aggregate materials from the sampling device;
(C1) depositing the sample in the metering hopper;
(C2) dispensing the sample at a controlled rate from the metering hopper onto the first screen of the gradation assembly while the frame is in the first frame position.

18. The method of claim 14 which includes:
(E) moving the frame from the first frame position to the second frame position, and vibrating the screens while the frame is in the second frame position.

19. The method of claim 18 wherein the screens are vibrated while the frame is in the second frame position by applying vibrations at a predetermined resonance frequency to each of the screens, with a first frequency being applied to induce resonance in the first screen in the stack, a second frequency being applied to induce resonance in the second screen and a third frequency being applied to induce resonance in the third screen.

* * * * *